US00PP17761P3

(12) United States Plant Patent
Korlipara

(10) Patent No.: US PP17,761 P3
(45) Date of Patent: May 29, 2007

(54) ***CAMPANULA* PLANT NAMED 'ROYAL WAVE'**

(50) Latin Name: ***Campanula* hybrid**
Varietal Denomination: Royal Wave

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 385 days.

(21) Appl. No.: 10/871,832

(22) Filed: Jun. 18, 2004

(65) Prior Publication Data

US 2005/0283876 P1 Dec. 22, 2005

(51) Int. Cl.
*A01H 5/00* (2006.01)

(52) U.S. Cl. ..... Plt./263

(58) Field of Classification Search ..... Plt./263, Plt./226

See application file for complete search history.

*Primary Examiner*—Kent Bell
(74) *Attorney, Agent, or Firm*—Klarquist Sparkman LLP

(57) ABSTRACT

A new and distinct hybrid of *Campanula* plant characterized by large cups of blue purple flowers with light centers and a mounding habit.

1 Drawing Sheet

Botanical classification: *Campanula* hybrid (parentage unknown).

Variety denomination: 'Royal Wave'.

The present invention relates to a new and distinct cultivar of *Campanula* plant and given the cultivar name of 'Royal Wave'. *Campanula* is in the family Campanulaceae. *Campanula* 'Royal Wave' is a tetraploid of *Campanula* 'Samantha' (parentage unknown). The tetraploidy was induced under laboratory conditions using 0.1% colchicine on Stage II plants in tissue culture. Subsequent offspring were trialed and *Campanula* 'Royal Wave' was selected as a single plant from these.

This new and unique *Campanula* is distinguished by:

1. Large, wavy, blue purple flowers with light centers.
2. Round habit.
3. Pollen and seed sterility resulting in long bloom time.

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
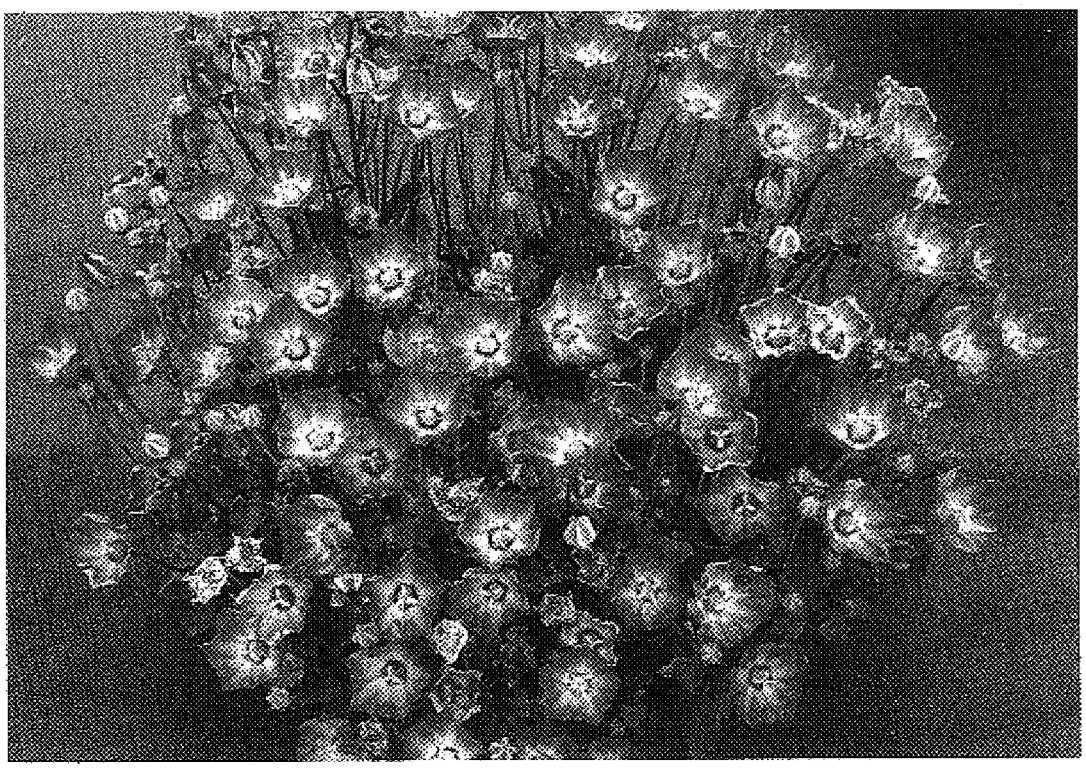
FIG. 1 shows *Campanula* 'Royal Wave' growing in the ground in the field in July in Canby, Oreg.
Figure 2:
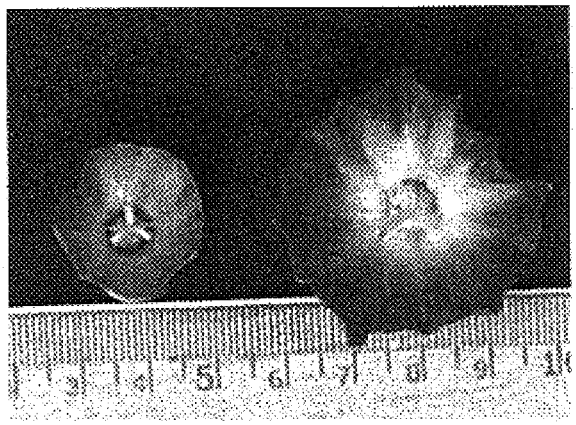
FIG. 2 shows a comparison of the flowers of *Campanula* 'Samantha' and *Campanula* 'Royal Wave', with *Campanula* 'Royal Wave' being the flower on the right.

The following is a detailed description of the new *Campanula* hybrid based on observations of one and a half year old specimen grown in a one gallon container in a shade house in Canby, Oreg. The color descriptions are all based on The Royal Horticultural Society Colour Chart.

Plant:

*Form.*—Tuft herbaceous perennial.
*Hardiness.*—USDA Zone 5 to 9.
*Size.*—23 cm tall and 35 cm wide.
*Habit.*—Compact, rounded.

Stem:

*Number.*—8 to 10, branching at each node, 8 main branches per stem, each of these branching about 4 times.
*Internode length.*—Varies from 1.5 cm to 4.5 cm.
*Size.*—14 to 17 cm long and up to 4 mm wide.
*Color.*—Yellow Green 146B.
*Vestiture.*—Hispid.

Leaf:

*Type.*—Simple.
*Arrangement.*—Alternate.
*Shape.*—Varies on placement. Lowest leaves on branches are cordate. Most leaves are deltoid. A few leaves at the very ends of the branches are lanceolate.
*Venation.*—Pinnate.
*Margins.*—Serrate, undulate.
*Apex.*—Acuminate.
*Base.*—Truncate, sometimes cordate and/or oblique.
*Blade size.*—Variable. 8 mm to 2.4 cm long and 5 mm to 2.5 cm wide.
*Vestiture.*—Sparsely hispid on margins and bottom side.
*Surface.*—Matte.
*Texture.*—Thin, leathery.
*Petiole length.*—Changes from 3.5 cm at the bottom of the stem to 3 mm at the top.
*Petiole vestiture.*—Sparsely hispid.
*Petiole color.*—Green 138B.
*Leaf color.*—Topside — Green 137A only darker. Bottom side — Closest to Green 137C.

Inflorescence:

*Type.*—Solitary and terminal.

*Peduncle.*—Size — 5 to 10 cm long and 1.5 mm wide. Vestiture — Glabrous. Color — Green 137A.

*Bloom period.*—July through August in Canby, Oreg.

Flower bud:

*Size.*—12 mm deep and 10 mm wide.

*Shape.*—Ovoid, star-shaped in cross section.

*Color.*—Violet Blue 91C to 91A where indented.

Flower:

*Type.*—Actinomorphic.

*Number of flowers.*—About 230 per plant.

*Shape.*—Broadly campanulate.

*Size.*—0.6 to 1 cm deep and 2.5 to 4 cm wide.

*Corolla lobes.*—5 lobes, cut to ½ ways to the base, lobes slightly overlapping, broadly ovate, 16 mm wide and 12 mm deep, acute tip, base narrowing slightly, margins entire.

*Color.*—Upper surface Violet Blue 93B with lighter centers Violet Blue 91C, lower surface Violet Blue 93B with lighter around the main vein, Violet Blue 91C.

*Calyx.*—Rotate in shape, 1.7 cm wide and deep, 5 lobes, each 7 mm long and 2 mm wide, with 4 to 8 teeth on the lobe margin and tip, cupped, tips acuminate.

*Calyx color.*—Green 137B to 137C.

*Stamen description.*—5 in number, 8 mm long, filaments White 155A, no pollen, male sterile.

*Pistil description.*—1, Yellow Green 145D overall, ovary above the corolla 3 mm deep, style 2 mm long, 3 branched reflexed stigma, each branch 5 mm long.

*Fragrance.*—Sweet.

*Lastingness.*—Each flower lasts for about 5 days on the plant.

Fruit and seed: None produced; plant is male and female sterile.

Diseases and pests: No diseases found of this new variety or on its parent plant. Many *Campanula* are susceptible to snails and slugs and aphids.

COMPARISON TO SIMILAR *CAMPANULA*

Compared to *Campanula* 'Samantha' (an unpatented plant), *Campanula* 'Royal Wave' has larger, thicker, and darker flowers with a lighter center. The habit is mounding only rather than mounding to weaving.

Compared to *Campanula carpatica* and its cultivars with blue purple flowers, *Campanula* 'Royal Wave' is a mounding-clumper rather than a slow creeper, with larger, thicker, and darker flowers. They have similar leaves in their margins and shape. The new variety has larger leaves.

I claim:

1. A new and distinct *Campanula* plant substantially as shown and described, characterized by large cups of blue purple flowers with light centers and a mounding habit.

* * * * *